(12) United States Patent
Ooi et al.

(10) Patent No.: US 9,983,308 B2
(45) Date of Patent: *May 29, 2018

(54) METHOD AND APPARATUS FOR LOCATING THE SURFACE OF SOLID GROWTH CULTURE MEDIA IN A PLATE

(71) Applicant: LBT Innovations Limited, Adelaide SA (AU)

(72) Inventors: Chong Kean Ooi, Glen Waverley (AU); Michael John Tomlinson, Ringwood East (AU); Leon Raj, Ferntree Gully (AU); Graeme John Cross, North Fitzroy (AU)

(73) Assignee: LBT Innovations Limited, Adelaide SA (AU)

( * ) Notice: Subject to any disclaimer, the term of this patent is extended or adjusted under 35 U.S.C. 154(b) by 232 days.

This patent is subject to a terminal disclaimer.

(21) Appl. No.: 14/169,630

(22) Filed: Jan. 31, 2014

(65) Prior Publication Data

US 2014/0146642 A1 May 29, 2014

Related U.S. Application Data (63) Continuation of application No. 12/520,969, filed as application No. PCT/AU2008/000014 on Jan. 11, 2008, now abandoned.

(30) Foreign Application Priority Data

Jan. 12, 2007 (AU) ................................ 2007900147

(51) Int. Cl.
*C12M 1/36* (2006.01)
*G01S 15/02* (2006.01)
(Continued)

(52) U.S. Cl.
CPC ............. *G01S 15/02* (2013.01); *C12M 23/50* (2013.01); *C12M 33/04* (2013.01); *G01B 21/16* (2013.01); *G01N 2035/0491* (2013.01)

(58) Field of Classification Search
CPC ...... C12M 23/10; C12M 23/50; C12M 33/02; C12M 33/04; G01N 35/1011; G01N 2035/1025

See application file for complete search history.

(56) References Cited

U.S. PATENT DOCUMENTS

| 3,455,788 A | 7/1969 | Curry et al. |
| 3,623,958 A | 11/1971 | Fitzgerald et al. |

(Continued)

FOREIGN PATENT DOCUMENTS

| CA | 1286621 C | 7/1991 |
| DE | 19520420 C2 | 12/1996 |

(Continued)

*Primary Examiner* — William H. Beisner
(74) *Attorney, Agent, or Firm* — Seager, Tufte & Whickhem LLP (57) ABSTRACT

A method for locating the surface of a solid growth culture medium in a plate in a plate work position, the plate work position including a sensor and having a datum level fixed in one dimension (z), the method including:
 placing the plate in the plate work position;
 using the sensor to sense the medium surface for the positioned plate and measuring the distance to the medium surface; and
 referencing the measured distance to the datum level to determine a surface positional reference, relative to the datum level, in one dimension (z) for the surface of the medium in the positioned plate.

12 Claims, 4 Drawing Sheets

(51) Int. Cl.
  *C12M 1/00* (2006.01)
  *C12M 1/26* (2006.01)
  *G01B 21/16* (2006.01)
  *G01N 35/04* (2006.01)

(56) References Cited

U.S. PATENT DOCUMENTS

| | | |
|---|---|---|
| 3,632,478 A | 1/1972 | Fink |
| 3,660,243 A | 5/1972 | Young |
| 3,778,351 A | 12/1973 | Rosov |
| 3,788,951 A | 1/1974 | von der Pfordten |
| 3,799,844 A | 3/1974 | Campbell et al. |
| 3,830,701 A | 8/1974 | Stussman et al. |
| 3,850,754 A | 11/1974 | Wilkins et al. |
| 3,935,075 A | 1/1976 | Perry et al. |
| 3,962,040 A | 6/1976 | Campbell et al. |
| 4,010,077 A | 3/1977 | Pardos |
| 4,102,748 A | 7/1978 | Vacanti |
| 4,144,135 A | 3/1979 | Sequeira |
| 4,170,861 A | 10/1979 | Snyder et al. |
| 4,287,301 A | 9/1981 | Astle |
| 4,613,573 A | 9/1986 | Shibayama et al. |
| 4,687,746 A | 8/1987 | Rosenberg et al. |
| 4,892,831 A | 1/1990 | Wong |
| 4,981,802 A | 1/1991 | Wylie et al. |
| 5,106,584 A | 4/1992 | Funakubo et al. |
| 5,206,171 A | 4/1993 | Dillon et al. |
| 5,629,201 A | 5/1997 | Nugteren et al. |
| 5,691,195 A | 11/1997 | Doleans et al. |
| 5,695,988 A | 12/1997 | Chong |
| 5,756,304 A | 5/1998 | Jovanovich |
| 6,291,234 B1 | 9/2001 | Raz et al. |
| 6,521,190 B1 | 2/2003 | Edens et al. |
| 6,617,146 B1 | 9/2003 | Naccarato et al. |
| 6,843,962 B2 | 1/2005 | Haslam et al. |
| 7,205,158 B2 | 4/2007 | Pankratz et al. |
| 7,709,268 B1 | 5/2010 | Edwards et al. |
| 7,829,021 B2 | 11/2010 | Hutchins et al. |
| 8,691,558 B2 * | 4/2014 | Gupta .................. C12M 33/02 435/286.3 |
| 2002/0064867 A1 | 5/2002 | Clark et al. |
| 2002/0120214 A1 | 8/2002 | Cole |
| 2007/0202564 A1 | 8/2007 | Glasson et al. |
| 2008/0318310 A1 | 12/2008 | Dufresne et al. |

FOREIGN PATENT DOCUMENTS

| | | |
|---|---|---|
| EP | 0 242 114 A2 | 10/1987 |
| FR | 2668495 A1 | 4/1992 |
| GB | 2025457 A | 1/1980 |
| GB | 2247076 A | 2/1992 |
| GB | 2255407 A | 11/1992 |
| JP | 62-028683 | 2/1987 |
| JP | 62-044166 | 2/1987 |
| JP | 62-155079 | 7/1987 |
| JP | 01191678 B | 8/1989 |
| JP | 02072898 A | 3/1990 |
| JP | 03049676 A | 3/1991 |
| JP | 03061476 A | 3/1991 |
| JP | 03133375 A | 6/1991 |
| JP | 03175996 A | 7/1991 |
| JP | 04234973 A | 8/1992 |
| JP | 04248980 A | 9/1992 |
| JP | 05225995 A | 9/1993 |
| JP | 05344535 A | 12/1993 |
| JP | 06225753 A | 8/1994 |
| JP | 06296481 A | 10/1994 |
| JP | 07067695 A | 3/1995 |
| JP | 07170970 A | 7/1995 |
| JP | 10004952 A | 1/1998 |
| JP | 10309199 A | 11/1998 |
| JP | 11346796 A | 12/1999 |
| JP | 2000-171360 | 6/2000 |
| JP | 2001149062 A | 6/2001 |
| JP | 2001149063 A | 6/2001 |
| JP | 2001153761 A | 6/2001 |
| JP | 2002098704 A | 4/2002 |
| JP | 3414431 B2 | 6/2003 |
| JP | 2005052069 A | 3/2005 |
| JP | 2005292044 | 10/2005 |
| JP | 2006-337245 | 12/2006 |
| JP | 2008166201 A | 7/2008 |
| WO | 8808024 A1 | 10/1988 |
| WO | 0166686 A1 | 9/2001 |
| WO | 2004022245 A1 | 3/2004 |
| WO | 2005/071055 A1 | 8/2005 |

* cited by examiner

METHOD AND APPARATUS FOR LOCATING THE SURFACE OF SOLID GROWTH CULTURE MEDIA IN A PLATE

REFERENCE TO RELATED APPLICATIONS

This application is a continuation of U.S. patent application Ser. No. 12/520,969, filed Dec. 14, 2009, which is a 371 of International Patent Application No. PCT/AU08/00014 filed Jan. 11, 2008, which is an international patent application that claims priority from Australian provisional patent application 2007900147 filed on 12 Jan. 2007, the contents of which are to be taken as incorporated herein by this reference.

FIELD OF THE INVENTION

The present invention relates generally to apparatus involved in the inoculation of solid growth culture media with a microbiological sample, and the subsequent streaking of the inoculum to produce isolated bacterial colonies, principally for diagnostic purposes in a laboratory, such as for medical diagnostic purposes. The present invention specifically relates to a method and an apparatus for locating the surface of a solid growth culture medium in a plate, to assist with a subsequent streaking operation, in an automated streaking apparatus. However, the invention is not to be limited to only that application.

BACKGROUND OF THE INVENTION

The isolation of individual colonies of micro-organisms (and in particular bacteria) is an important procedure in many microbiological laboratories. Traditionally, this isolation of bacteria has been performed manually by skilled laboratory technicians who first dispense a microbiological sample onto the surface of a solid growth culture medium, such as agar in a Petri dish (which will hereafter simply be referred to as a "medium" in an "agar plate" or simply in a "plate"), followed by the use of a hand-tool to spread the sample across the surface of the medium (called "streaking").

The hand-tool typically includes a terminal loop to make multiple streaks of increasing dilution of the inoculum across the medium. The streaks of increasing dilution tend to provide, generally towards the tail of the streaks, a number of single cells that allow for the growth of isolated microbiological colonies after incubation. These isolated colonies may then be analysed for colony morphology, and may undergo staining and other procedures which are necessary for determining, for example, the genus, the species and the strain of the previously unidentified organism.

Such inoculation and streaking is highly repetitious and in many pathology diagnostic microbiology laboratories is usually conducted in very high volumes, such as in volumes as high as 1,000 to 15,000 plates per day. It is tedious and laborious work that therefore is prone to error and inaccuracies. It is quite obviously work that would lend itself to either partial or full automation.

The literature is replete with suggestions for how best to automate these laboratory functions, yet very few of these suggestions have ever actually found success in a commercial laboratory environment. It therefore appears that the successful enablement of suitable laboratory apparatus has to date, for most, proved elusive.

Three recent suggestions for the automation of these laboratory functions can be found in the following documents; U.S. Pat. No. 4,981,802 (C. Wylie et al) titled "Method and Apparatus for Streaking a Culture Medium", U.S. Pat. No. 6,617,146 (F. Naccarato et al) titled "Method and Apparatus for Automatically Inoculating Culture Media With Bacterial Specimens From Specimen Containers", and international patent publication WO2005/071055 (Medvet Science Pty Ltd) titled "Microbial Streaking Device" (licensed to the present applicant).

The Wylie and Naccarato patents describe automated and semi-automated apparatus that utilize re-usable streaking tools similar to the hand streaking tools mentioned above, without describing a suitable system or mechanism for that apparatus to determine, in three dimensional space, the precise location of the surface of the medium.

While the Medvet Science publication describes the use of a new form of streaking tool, being a streaking applicator that includes a line of spaced apart contact surfaces (for contact with the surface of solid growth media), the contact surfaces being resiliently flexibly supported by a common support member, this new streaking tool still of course requires placement upon the surface of the medium. The Medvet Science publication suggests that this can be dealt with providing the apparatus with a pressure sensing device to determine when the tool is suitably upon the surface.

It will be appreciated that the height of medium, such as agar, within a plate will fluctuate depending upon many factors. For example, not only do different plate and solid growth culture medium suppliers invariably produce agar plates, for example, with a wide variety of surface heights from one supplier to the next, but even the same suppliers tend to supply their own plates with varying heights of media. Also, different compositions and ages of media used for this purpose tend also to produce plates with different media surface heights. Therefore, and due to such fluctuations in height, it is generally not possible for an automated streaking apparatus to rely upon the height of the surface of media in all plates to be the same.

It is therefore not feasible for an inoculating device, for example, of such an automated apparatus to rely on being able to place inoculum upon the surface of media at the same location in three dimensional space for every plate to be processed thereby, and significant difficulties and complexities can be introduced in an apparatus that does. As another example, there are also potential difficulties and complexities for a streaking device of such an automated apparatus in trying to place a streaking tool upon the surface (so as to spread the inoculum rather than to gouge the surface) of media at the same location for every plate in three dimensional space.

In relation to an inoculating device, it will be appreciated that the incorrect location of a dispensing tip in the z dimension (height) will give rise to the inoculum being dispensed from too high (and thus not dispensing as required), or there being contact with the surface such that the tip gouges the surface of the medium. In relation to a streaking device, incorrect location of the contact surfaces in the z dimension (height) will give rise to there either being no contact with the inoculum whatsoever, or there being too much contact such that the streaking tool also gouges tracks in the surface of the medium.

It is an aim of the present invention to provide both a method and an apparatus capable of locating the surface of the medium in a plate prior to, for example, inoculation and streaking of that plate. In this respect, and as foreshadowed above, it is also an aim of the present invention for the method and apparatus to find use in laboratory situations other than the inoculation and streaking situations described above. Indeed, the method and apparatus of the present invention may find use in any laboratory to simply provide a process, for any purpose, for locating the surface of solid growth culture medium in a plate.

Before turning to a summary of the present invention, it must be appreciated that the above description of the prior art has been provided merely as background to explain the context of the invention. It is not to be taken as an admission that any of the material referred to was published or known, or was a part of the common general knowledge in Australia or elsewhere.

It is also useful to provide an explanation of some of the terms that will be used to define the spatial relationship of the apparatus and various parts thereof. In this respect, spatial references throughout this specification will generally be based upon a plate ultimately being inoculated and streaked in an automated streaking apparatus in an upright orientation, with the surface of the medium in the plate being generally flat and horizontal. With this environment as the basis, the apparatus and some parts thereof may then be defined with reference to the "horizontal", allowing further references to "upper" or "upwardly" and "lower" or "downwardly", and also to the "vertical". In this respect, the traditional geometric spatial reference to x, y and z dimensions, and then to the x direction (or axis), the y direction (or axis) and the z direction (or axis), will also be adopted, with the x and y directions lying generally horizontally and the z direction lying generally vertically.

Finally, some aspects of the present invention that may ultimately be claimed in isolation (and not in an in-use environment), may nonetheless be difficult to describe and understand in isolation. Thus, some of the following description does describe the invention and its embodiments in such an in-use environment (for example, in association with a plate carrying medium within an automated streaking apparatus). Of course, it must be appreciated that the use of such description, and the use of the abovementioned spatial relationships, to define the present invention, is not to be seen as a limitation and certainly is not to be seen as a limitation only to the in-use environment, unless that intention is clearly stated.

SUMMARY OF THE INVENTION

The present invention provides a method for locating the surface of a solid growth culture medium in a plate in a plate work position, the plate work position including a sensor and having a datum level fixed in one dimension (z), the method including:
  placing the plate in the plate work position;
  using the sensor to sense the medium surface for the positioned plate and measuring the distance to the medium surface; and
  referencing the measured distance to the datum level to determine a surface positional reference, relative to the datum level, in one dimension (z) for the surface of the medium in the positioned plate.

It will thus be appreciated that the surface of a medium in a plate, which plate is in its normal, generally horizontal orientation, can thus be located in at least the z dimension by virtue of the determination of the surface positional reference. This effectively determines the height of the medium in the plate, at least with reference to the datum level. In a preferred form, the datum level will be a level (or a surface) that forms a part of a plate platform upon which the plate can be clamped and supported. Therefore, in this preferred form, the determination of the surface positional reference effectively determines the height of the medium with reference to the plate platform upon which it rests. This is useful in that the referencing of the medium in this manner then permits another, possibly unrelated, apparatus to operatively interact with the surface of the medium with some precision, as would be required where the invention is used in an automated streaking apparatus (as will be outlined below).

In one form of the invention, the medium height is not sensed by the sensor across its full extent, but is only sensed in a sensing region which is a part of that full extent. For example, in one form, the method senses the medium surface within a sensing region and measures the distance to the medium surface within that sensing region. In practice, this measured distance is likely to be an average over the area of the sensing region, given the likelihood of the distance varying across that region due to the height of the surface varying due to surface imperfections and the like.

However, and as mentioned above, a preferred use for the method of the present invention is in the inoculation and streaking of the medium in the plate, which generally requires the determination of the location in three dimensional space of a line across the surface of the medium, and not just the determination of a point (or region) in one dimensional space, for the purpose of spreading an inoculum along that line and then locating a streaking tool along that line (sometimes referred to as an "action line").

The present invention thus also provides a method for locating the surface of a solid growth culture medium in a plate in a plate work position, the plate work position including a sensor and having a notional action line fixed in two dimensions (x, y) in a predetermined position and having a datum level fixed in one dimension (z), the method including:
  placing the plate in the plate work position;
  using the sensor to sense the medium surface within a sensing region for the positioned plate and measuring an average distance to the medium surface within that sensing region;
  referencing the measured distance to the datum level to determine a surface positional reference relative to the datum level in one dimension (z) for the surface of the medium in the positioned plate; and
  using the surface positional reference and the notional action line to determine a line in three dimensions (x, y, z) that is representative of a line across the surface of the medium in the positioned plate.

In another preferred form of the present invention, the method includes the additional step of setting an upper detection limit and a lower detection limit, in some forms with the upper detection limit above the datum level and the lower detection limit below the datum level, to define a detection range between the upper and lower limits. The use of such a detection range can be adopted in conjunction with either the method for the determination of the surface positional reference alone or the method for the determination of the representative surface line from the surface positional reference.

A detection range of this type is an arbitrary range and thus the upper and lower limits of the detection range can be set arbitrarily. A detection range can provide a calibration opportunity and allows the identification of, for example, multiple calibration sub-ranges to be applied within the detection range. For example, in some forms of the invention it may not be necessary or desirable for the method to be able to determine if a plate positioned in the plate work position still includes its lid thereon, or perhaps has been placed in the plate work position upside down. Thus, by adopting a narrow detection range, where the upper limit is only just above where the surface of the medium is expected to be, and the lower limit is only just below where the surface of the medium is expected to be, the sensor will not function if the detectable height of the plate in the plate work position is outside this narrow range, due to the sensor detecting either the surface of the plate lid or the surface of the plate bottom.

Conversely, there may be situations where it is desirable for the method to be able to provide an alarm, for example, if a lidded or empty plate is placed in the plate work position. If a suitably broad enough detection range has been set, the sensor will thus sense the presence of the lid wall or the bottom wall, and will measure the distance to that surface rather than to the surface of medium in the plate. Thus, by the provision of a suitably broad detection range with calibration sub-ranges for alarm conditions (lidded plate or empty plate, for example) and for non-alarm conditions (de-lidded upright plate), the calibration sub-ranges can cause the identification (by virtue of the determination of the surface positional reference and its presence in one of the alarm calibration sub-ranges) of an alarm condition, as well as allow for the proper functioning of the method.

For example, and depending upon the likely thicknesses of plates and the likely height of the medium used therein, in one form the detection range can be set at about 30 mm, with the upper limit set 20 mm above the datum level and the lower limit set 10 mm below the datum level. In this form, and with reference to typical plates, a lidded plate (in either orientation) may produce a surface positional reference at about 7 mm below the upper limit, a de-lidded upright plate may produce a surface positional reference (for its medium surface) at about 14 mm below the upper limit, and a de-lidded but empty plate may produce a surface positional reference at about 18 mm below the upper limit (which is only the thickness of the bottom wall of the plate above the datum level).

The present invention thus also provides a method for locating the surface of a solid growth culture medium in a plate in a plate work position, the plate work position including a sensor and having a datum level fixed in one dimension (z), the method including:
  setting an upper limit and a lower limit to define a detection range between the upper and lower limits;
  placing the plate in the plate work position;
  using the sensor to sense, within the detection range, the medium surface for the positioned plate and measuring the distance to the medium surface; and
  referencing the measured distance to the datum level to provide a surface positional reference relative to the datum level in one dimension (z) for the surface of the medium in the positioned plate.

Further, the present invention may also provide a method for locating the surface of a solid growth culture medium in a plate in a plate work position, the plate work position including a sensor and having a notional action line fixed in two dimensions (x, y) in a predetermined position and having a datum level fixed in one dimension (z), the method including:
  setting an upper limit and a lower limit to define a detection range between the upper and lower limits;
  placing the plate in the plate work position;
  using the sensor to sense the medium surface, within the detection range, within a sensing region for the positioned plate and measuring an average distance to the medium surface within that sensing region;
  referencing the measured distance to the datum level to determine a surface positional reference relative to the datum level in one dimension (z) for the surface of the medium in the positioned plate; and
  using the surface positional reference and the notional action line to determine a line in three dimensions (x, y, z) that is representative of a line across the surface of the medium in the positioned plate.

As mentioned above, preferably the datum level is fixed and is thus a known parameter in the apparatus. In one form of the invention, the datum level is fixed as the uppermost surface of a platform configured to hold the plate in the plate work position, the uppermost surface thus being that surface immediately below the plate. With this in mind, the platform is itself preferably fixed in the z direction, such that its location in the z direction is constant and known, regardless of whether the platform is required to move in the x or y directions as a part of its normal operation.

It may thus be beneficial to further include as a part of the present invention, an ability to regularly verify that this location has not altered, such as by being able to verify this on a daily, weekly or monthly basis, or being able to verify this prior to every operational run of the method and apparatus of the invention, or even prior to (although this is unlikely) each measurement being taken. Indeed, it will be appreciated that even normal mechanical operational vibrations (or temperature variations) may cause the location of the datum level in the z direction to alter (even slightly alter), which could have an impact on the precision of operation of the method and apparatus.

The sensor can be any type of sensor that is able to be programmed and controlled to sense the presence of a surface in the manner described above and then to measure the distance to the sensor, ideally from a fixed datum point that is a part of the sensor. The sensor may for example be a laser sensor or an ultrasonic sensor. Preferably, the sensor includes a programmable controller that is able to additionally perform the referencing tasks mentioned above.

In a preferred form, the sensor is an ultrasonic sensing device that includes an ultrasonic beam focusing element that is capable of providing a focused beam on the medium surface, preferably within the sensing region mentioned above. In the form of the invention where the representative line is to be determined from the surface positional reference, this sensing region is thus preferably central to the predetermined notional action line also mentioned above.

The sensor is preferably rigidly mounted to a main frame, thereby defining the general location of the plate work position. In this form, the sensor is ideally mounted so that it is above the plate work position and is operatively adjacent a positioned plate held immediately therebelow in a plate platform, the positioned plate having its medium surface open upwardly.

Thus, the present invention also provides an apparatus for locating the surface of a solid growth culture medium in a plate in a plate work position, the plate work position including a sensor and having a datum level fixed in one dimension (z), wherein the sensor is capable of sensing the medium surface for the positioned plate and measuring the distance to the medium surface, the apparatus also including means for referencing the measured distance to the datum level to determine a surface positional reference, relative to the datum level, in one dimension (z) for the surface of the medium in the positioned plate.

The present invention further provides an apparatus for locating the surface of a solid growth culture medium in a plate in a plate work position, the plate work position including a sensor and having a notional action line fixed in two dimensions (x, y) in a predetermined position and having a datum level fixed in one dimension (z), wherein the sensor is capable of sensing the medium surface within a sensing region for the positioned plate and measuring an average distance to the medium surface within that sensing region, the apparatus also including means for referencing the measured distance to the datum level to determine a surface positional reference relative to the datum level in one dimension (z) for the surface of the medium in the positioned plate and then using the surface positional reference and the notional action line to determine a line in three dimensions (x, y, z) that is representative of a line across the surface of the medium in the positioned plate.

Further, the present invention also provides an apparatus for locating the surface of a solid growth culture medium in a plate in a plate work position, the plate work position including a sensor and having a datum level fixed in one dimension (z), wherein the sensor has an upper limit and a lower limit to define a detection range between the upper and lower limits, and is capable of sensing, within the detection range, the medium surface for the positioned plate and measuring the distance to the medium surface, the apparatus including means for referencing the measured distance to the datum level to provide a surface positional reference relative to the datum level in one dimension (z) for the surface of the medium in the positioned plate.

Further still, the present invention may also provide an apparatus for locating the surface of a solid growth culture medium in a plate in a plate work position, the plate work position including a sensor and having a notional action line fixed in two dimensions (x, y) in a predetermined position and also having a datum level fixed in one dimension (z), wherein the sensor has an upper limit and a lower limit to define a detection range between the upper and lower limits, and is capable of sensing the medium surface, within the detection range, within a sensing region for the positioned plate and measuring an average distance to the medium surface within that sensing region, the apparatus including means for referencing the measured distance to the datum level to determine a surface positional reference relative to the datum level in one dimension (z) for the surface of the medium in the positioned plate, and then using the surface positional reference and the notional action line to determine a line in three dimensions (x, y, z) that is representative of a line across the surface of the medium in the positioned plate.

Also, it will of course be appreciated that the surface positional reference, and the representative line, for the surface of a medium in a positioned plate will be specific to the medium in that positioned plate only, and may be (and is actually likely to be) a different surface positional reference and representative line compared to the surface of the next plate processed in the plate work position.

Finally, it is envisaged that the method and apparatus of the present invention will additionally find use with half-plates (often referred to as bi-plates) where the two halves of a plate are separated by an upstanding diametric wall, and each half containing a medium whose height is to be determined in the manner described above. In this situation, the methods described above can be modified to also permit detection of, or confirmation of, the location of the upstanding wall, to then trigger the operation of the method of the invention twice in relation to that plate, on both halves. Alternatively, the method could of course be modified to simply permit the apparatus to be otherwise informed of the existence of a bi-plate, to subsequently trigger operation of the method on both halves.

As evident from the above, the method and apparatus of the present invention is primarily suitable for use with an automated streaking apparatus, ideally of the type generally described in the present applicant's international patent application filed on 11 Jan. 2008 titled "Method and Apparatus for Inoculating and Streaking a Medium in a Plate", claiming priority from Australian provisional patent application 2007900146, the full content of which is hereby incorporated by reference.

In one form, the inoculating device will include a reasonably typical pipette device mounted to a robot system so as to be movable in the z direction and at least one of the x,y directions (using the directional terminology adopted above). The pipette device preferably includes a disposable dispensing tip releasably secured to a pipette body, secured in a manner that permits easy disposal of the tip once inoculation has been affected.

The inoculating device is preferably programmable for various inoculum volumes, and includes a positional height (z direction) referencing system capable of determining in three dimensional space the height of the location of the dispensing tip relative to the locating datum surface of the platform mentioned above, and of course relative to the notional action line mentioned above.

The inoculating device may additionally include means for separately imaging the dispensing tip during various of the abovementioned range of actions, so as to be able to (for example) visually or electronically monitor for the presence of a tip prior to sampling. In this respect, in one form of the present invention, this imaging means may additionally provide the positional height (z direction) referencing system mentioned above.

The pipette robot system of the inoculating device is preferably able to move the pipette device to access the dispensing tip supply, a biological sample station, the plate work position in the inoculating and streaking station, and also a tip waste disposal chute, whilst also including suitable tip securing means that allows for a dispensing tip to be secured, used to obtain and hold sample, dispense sample, and then dispose of the used tip. It will thus be appreciated that the pipette robot system of the inoculating device will move the pipette through this entire range of actions for each of the plates being processed by the apparatus.

For present purposes, one form of that streaking apparatus generally includes:
(a) a plate supply capable of storing raw plates in an inverted orientation;
(b) a plate transfer feed mechanism capable of obtaining an inverted raw plate from the plate supply, de-lidding the raw plate and orientating the raw plate such that its bottom is lowermost, and transferring the orientated and de-lidded raw plate to a plate work position in an inoculating and streaking station;
(c) the apparatus of the present invention, being a sensor capable of locating the surface of the medium in a positioned plate prior to inoculation and streaking of that plate;
(d) an inoculating device capable of dispensing inoculum on the surface of the medium in the positioned plate;
(e) a streaking device capable of obtaining a streaking applicator from a streaking applicator supply and then moving the streaking applicator such that its line of spaced apart contact surfaces contacts the surface of the medium in the positioned plate, prior to rotation of the positioned plate for streaking;

(f) a plate store capable of storing processed plates in an inverted orientation; and (g) a plate transfer store mechanism capable of retrieving a processed plate from the plate work position, re-orientating and re-lidding the processed plate, and transferring the processed plate to the plate store.

Thus, in one form (although not the only form thereof), the method and apparatus of the present invention is intended to be suitable for use as the sensor for the plate work position of the above described automated streaking apparatus.

BRIEF DESCRIPTION OF THE DRAWINGS

Having briefly described the general concepts involved with the present invention, a preferred embodiment will now be described that is in accordance with the present invention. However, it is to be understood that the following description is not to limit the generality of the above description.

In the drawings.

DESCRIPTION OF A PREFERRED EMBODIMENT

Figure 1:
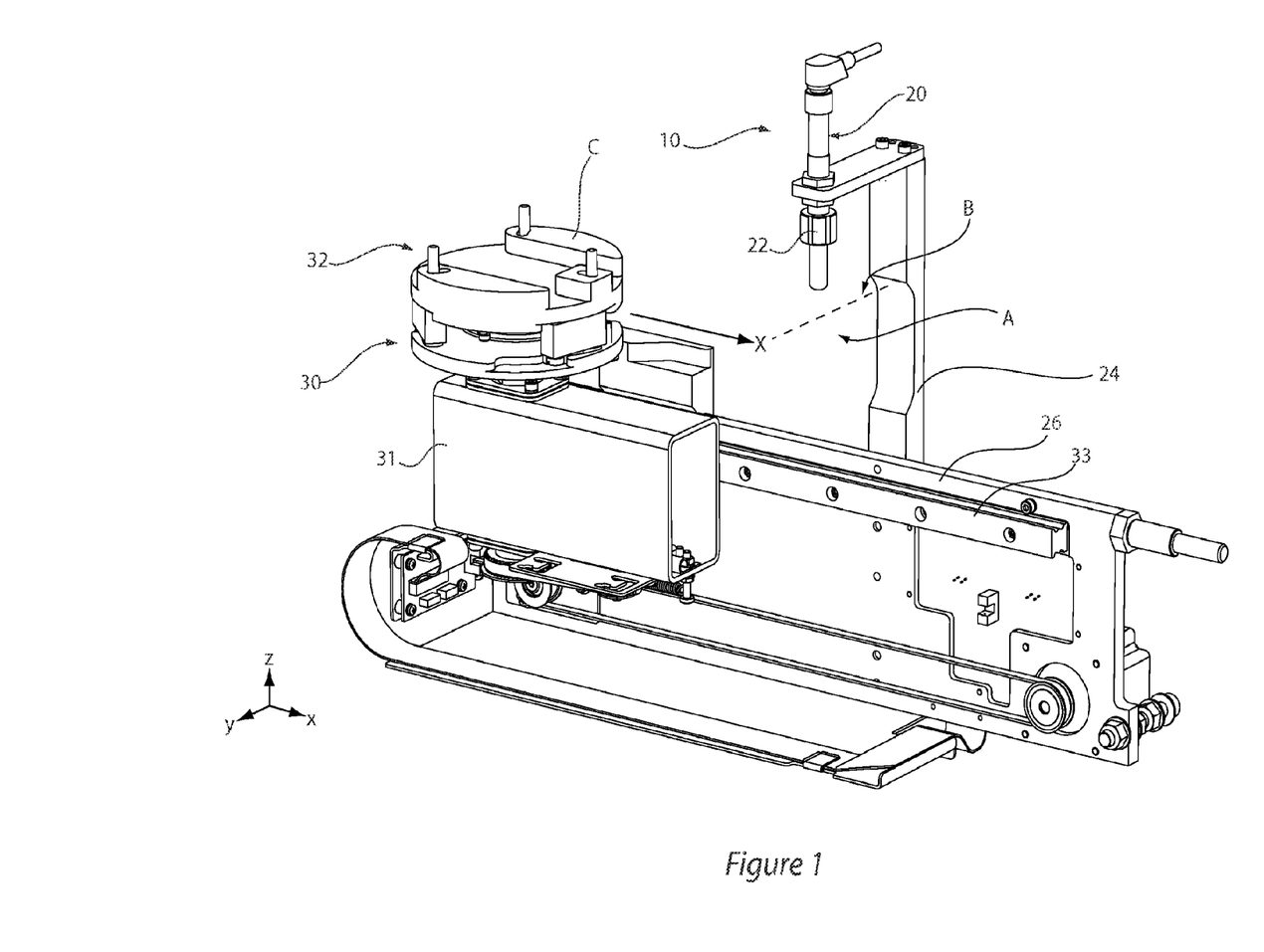
FIG. 1 is a perspective view from above of an apparatus in accordance with a preferred embodiment of the present invention, showing a plate platform near a plate work position.
Figure 2:
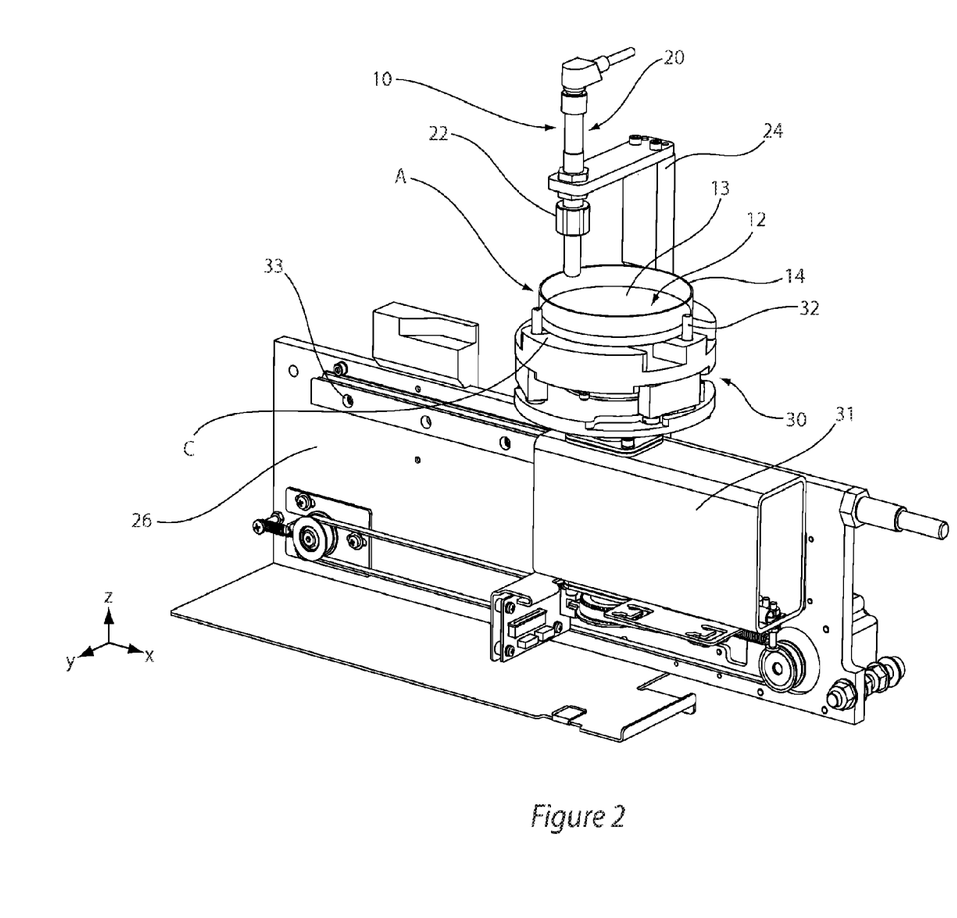
FIG. 2 is a perspective view from above of the apparatus of FIG. 1, showing a plate held in the plate platform in the plate work position.

Illustrated in FIGS. 1 and 2 is an apparatus 10 for locating the surface of a solid growth culture medium 12 having a surface 13 in a plate 14 in a plate work position A, with the medium 12 and the plate 14 not shown in FIG. 1. FIG. 1 shows a plate platform 30 able to receive a plate 14 in a centralized and clamped position in order to move the plate in the direction of arrow X into the plate work position A. The plate platform 30 is mounted on a support 31 for sliding movement along a guide rail 33 in response to suitable controllers. The plate platform 30 includes a plate clamping member 32 in the form of three movable lugs operated by a camming device (not shown), which lugs are preferably also able to function as a plate centralizing means for centralizing the position of the plate 14 on the platform 30. This can be useful for subsequent operations with the plate 14.

In this embodiment of the invention, which is an embodiment for use with an automated streaking apparatus of the type identified above, the plate work position A includes a notional action line B (shown by a broken line in FIG. 1) fixed in two dimensions (x, y) in a predetermined position. However, and also as explained above, in some embodiments of the invention, where it may not be necessary to determine a line, located in three dimensional space, for the surface of a medium (represented by a line across its surface such as is illustrated as line D in FIG. 3 for this embodiment), there will be no need for predetermination of the notional action line B.

In this embodiment though, the notional action line B is fixed in two dimensions (x, y) in a predetermined position. This action line B is herein referred to as being a "notional" action line given that it will not be a visible action line and also will not have a determined position in three dimensional space until the location of the surface 13 of the medium 12 in the plate 14 is determined.

The plate work position A includes a datum level C, which in FIG. 1 is shown as the uppermost surface upon the plate platform 30 (eventually to be located, as is evident in FIG. 2, within the plate work position A).

The apparatus 10 includes a sensor 20 that includes an ultrasonic sensing device 22 having an ultrasonic beam focusing element that is capable of providing a focused beam on the medium surface 12, preferably within a sensing region (not identified in FIGS. 2 and 3) that is central to the predetermined notional action line B. The sensor 20 is rigidly mounted via a sensor support arm 24 to a main frame 26, thereby defining the general location of the plate work position A. In this form, the sensor 20 is ideally mounted so that it is above the plate work position A and is operatively adjacent the plate 14 held immediately therebelow in the plate platform 30, the plate 14 having its surface 13 open upwardly as is evident in FIG. 3.

Figure 3:
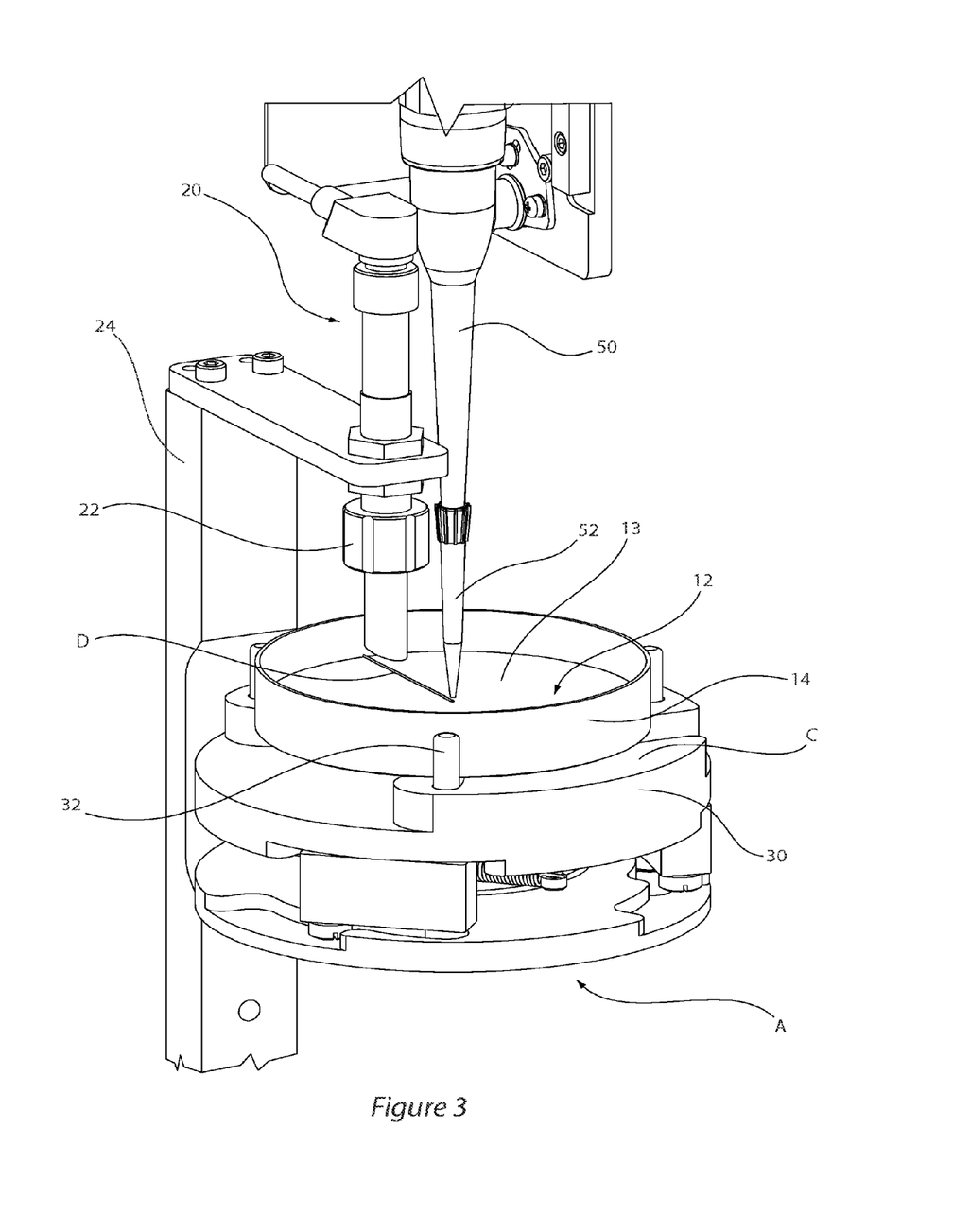
FIG. 3 is a perspective view from above of a part of the apparatus of FIG. 1, showing the apparatus in use and a three dimensional action line.

With reference to FIG. 3, the method of this embodiment of the present invention thus requires the sensor 20 to sense the medium surface 13 for the positioned plate 14 and measure the distance to the medium surface 13. Then, the measured distance is referenced to the datum level C to determine a surface positional reference relative to the datum level C in one dimension (z) for the surface 13 in the positioned plate 14. In this manner, it will be appreciated that the surface 13 can thus be located in at least the z dimension by virtue of the determination of this surface positional reference. This effectively determines the height of the medium 12 in the plate 14, at least with reference to that datum level C. In this respect, and as can be seen in the figures, the datum level C is a surface that forms a part of the plate platform 30 upon which the plate 14 is clamped and supported. Therefore, in this embodiment, the determination of the surface positional reference effectively determines the height of the medium 12 with reference to the plate platform 30 upon which it rests.

This surface positional reference can then be used, together with the notional action line B (from FIG. 1) to determine the line D in three dimensions (x, y, z) that is representative of a line across the surface 13 in the positioned plate.

Following location of the surface in this manner, an inoculating device 50 can be brought to the plate work position A to inoculate the surface 12 in the manner described above. By having previously determined, by suitable means, the location and orientation of the dispensing tip 52 on the inoculating device 50, the dispensing tip 52 can be brought as close as desired to the representative line D (and thus the surface 12) to dispense inoculum therealong. The same benefits are of course available for operatively interacting a streaking device (not shown) having a streaking tool (also not shown) upon the surface 13.

As mentioned above, in an embodiment of present invention, there can be included the additional step of setting an upper detection limit and a lower detection limit, in some forms with the upper detection limit above the datum level C and the lower detection limit below the datum level C, to define a detection range between the upper and lower limits. The use of such a detection range can be adopted in conjunction with either the method for the determination of the surface positional reference (alone) or the method for the determination of the representative surface line D (as has been illustrated in FIGS. 1 to 3 for this embodiment of the invention) from the surface positional reference.

Figure 4:
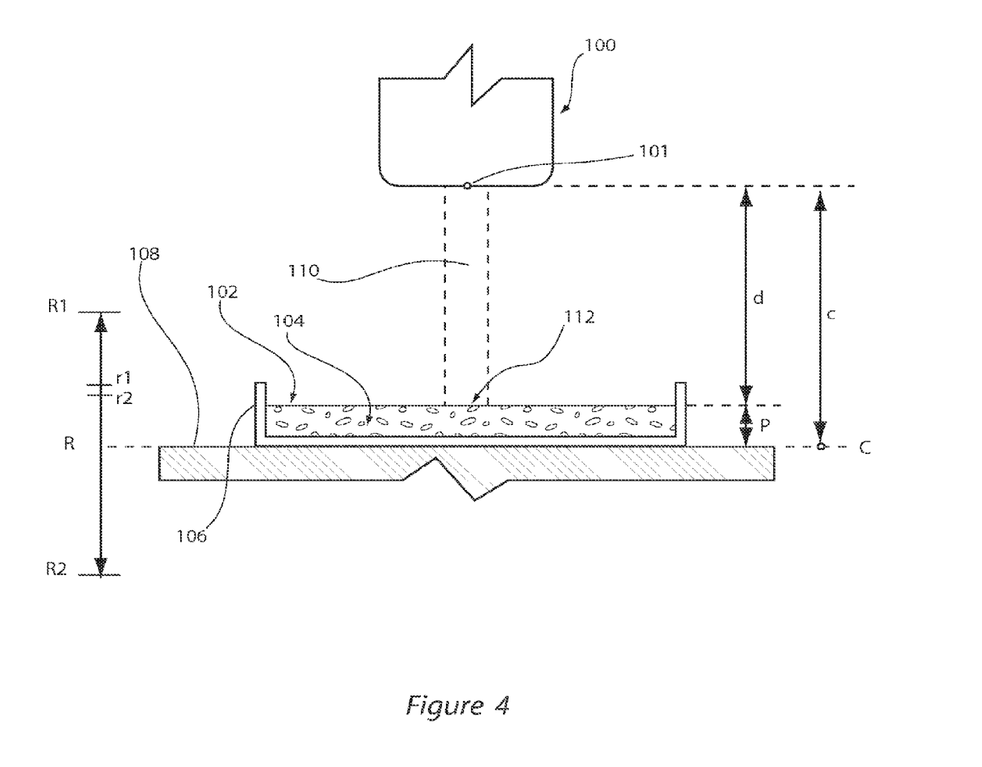
FIG. 4 is a schematic illustration of the apparatus of FIG. 1 in use, showing the various geometric and mathematical relationships.

In order to assist with an explanation of the use of such a detection range, but also to assist with an understanding of the mathematical and geometric processes described above, reference is made to the schematic illustration of FIG. 4 (which generally utilizes different reference numerals to those used above for FIGS. 1 to 3).

In FIG. 4, there is shown a sensor 100 located above the surface 102 of a medium 104 in a plate 106. The plate 106 is shown seated upright upon a plate platform 108 that is used to provide a fixed datum level C. The sensor 100 is an ultrasonic sensor that emits an acoustic signal towards the surface 102 via the beam 110 to form a sensing region 112.

The sensor is operated to measure the distance d to the surface 102 from its fixed datum point 101, the distance d being calculated by the sensor 100 as an average of the distances across the sensing region 112. The measured distance d is then referenced to the datum level C, which is thus a known distance c from the sensor 100. This referencing permits the determination of a surface positional reference p, relative to the datum level C, in one dimension (z) for the surface 102 in the positioned plate 106. In this embodiment, the surface positional reference p is a very close approximation to the depth of the medium 104 in the plate 106, due to the use of the uppermost surface of the plate platform 108 as the datum level C, the measure only being an approximation due to the thickness of the plate bottom.

Nonetheless, by locating the surface 102 in this manner (or by taking the additional step of locating the surface 102 with reference to a line in three dimensions), it then becomes possible to bring to the surface 102 other apparatus, such as the inoculation and streaking devices mentioned above, such that they can engage or operatively interact with the surface as required due to this knowledge of the location of the surface.

Also illustrated in FIG. 4 is a detection range R having an upper limit $R_1$ and a lower limit $R_2$, which have been set arbitrarily at levels above and below the datum level C. In this respect, it will be appreciated that the detection range R could have been arbitrarily set at levels $r_1$ and $r_2$ for a situation where it is not necessary or desirable to determine if, for example, the plate 106 still included its lid thereon, or perhaps had been placed on the platform 108 empty of medium. In that situation, and with such a narrow detection range, where the upper limit $r_1$ is only just above the surface 102 and the lower limit $r_2$ is only just below the surface 102, the sensor 100 will not function if the detectable upwardly exposed surface of a plate is outside this narrow range, due to the sensor 100 detecting either the surface of the plate lid or the surface of the plate bottom.

However, in this embodiment, it is desirable to provide an alarm in both of these situations and thus a relatively broad enough detection range R has been set. Thus, in this embodiment, the sensor 100 is able to sense the presence of the lid wall or the bottom wall as they will be within the detection range set by the upper limit $R_1$ and the lower limit $R_2$, and will measure the distance to that surface rather than to the surface of the medium in the plate. By the provision of calibration sub-ranges between $r_1$ and $R_1$ and between $r_2$ and $R_2$, such calibration sub-ranges can cause the identification (by virtue of the determination of the surface positional reference and its presence in one of the alarm calibration sub-ranges) of an alarm condition, as well as allowing for the proper functioning of the method.

Certain embodiments or configurations of the present invention may be described by the following aspects:

1. A method for locating the surface of a solid growth culture medium in a plate in a plate work position, the plate work position including a sensor and having a datum level fixed in one dimension (z), the method including:
   placing the plate in the plate work position;
   using the sensor to sense the medium surface for the positioned plate and measuring the distance to the medium surface; and
   referencing the measured distance to the datum level to determine a surface positional reference, relative to the datum level, in one dimension (z) for the surface of the medium in the positioned plate.

2. A method according to aspect 1, wherein the surface of a medium in a plate, which plate is in its normal, generally horizontal orientation, is located in at least the z dimension by virtue of the determination of the surface positional reference.

3. A method according to aspect 1 or aspect 2, wherein the datum level is a surface that forms a part of a plate platform upon which the plate can be clamped and supported.

4. A method according to any one of aspects 1 to 3, wherein the determination of the surface positional reference determines the height of the medium with reference to the plate platform upon which it rests.

5. A method according to any one of aspects 1 to 4, wherein the medium is sensed in a sensing region, such that the measured distance is an average over the area of the sensing region.

6. A method for locating the surface of a solid growth culture medium in a plate in a plate work position, the plate work position including a sensor and having a notional action line fixed in two dimensions (x, y) in a predetermined position and having a datum level fixed in one dimension (z), the method including:
   placing the plate in the plate work position;
   using the sensor to sense the medium surface within a sensing region for the positioned plate and measuring an average distance to the medium surface within that sensing region;
   referencing the measured distance to the datum level to determine a surface positional reference relative to the datum level in one dimension (z) for the surface of the medium in the positioned plate; and
   using the surface positional reference and the notional action line to determine a line in three dimensions (x, y, z) that is representative of a line across the surface of the medium in the positioned plate.

7. A method for locating the surface of a solid growth culture medium in a plate in a plate work position, the plate work position including a sensor and having a datum level fixed in one dimension (z), the method including:
   setting an upper limit and a lower limit to define a detection range between the upper and lower limits;
   placing the plate in the plate work position;
   using the sensor to sense, within the detection range, the medium surface for the positioned plate and measuring the distance to the medium surface; and
   referencing the measured distance to the datum level to provide a surface positional reference relative to the datum level in one dimension (z) for the surface of the medium in the positioned plate.

8. A method according to aspect 7, wherein the upper detection limit is above the datum level and the lower detection limit is below the datum level.
9. A method according to aspect 7 or aspect 8, wherein the detection range is provided with calibration sub-ranges.
10. A method according to aspect 9, wherein the calibration sub-ranges identify alarm conditions.
11. A method according to aspect 10, wherein the alarm conditions are where a plate positioned in the plate work position still includes its lid thereon or has been placed in the plate work position upside down.
12. A method according to aspect 11, wherein the detection range is set at about 30 mm, with the upper limit set 20 mm above the datum level and the lower limit set 10 mm below the datum level.
13. A method for locating the surface of a solid growth culture medium in a plate in a plate work position, the plate work position including a sensor and having a notional action line fixed in two dimensions (x, y) in a predetermined position and having a datum level fixed in one dimension (z), the method including:
setting an upper limit and a lower limit to define a detection range between the upper and lower limits;
placing the plate in the plate work position;
using the sensor to sense the medium surface, within the detection range, within a sensing region for the positioned plate and measuring an average distance to the medium surface within that sensing region;
referencing the measured distance to the datum level to determine a surface positional reference relative to the datum level in one dimension (z) for the surface of the medium in the positioned plate; and
using the surface positional reference and the notional action line to determine a line in three dimensions (x, y, z) that is representative of a line across the surface of the medium in the positioned plate.
14. A method according to any one of aspects 1 to 13, wherein the sensor is an ultrasonic sensing device that includes an ultrasonic beam focusing element that is capable of providing a focused beam on the medium surface.
15. A method according to any one of aspects 1 to 14, wherein the sensor is rigidly mounted to a main frame, thereby defining the general location of the plate work position.
16. A method according to any one of aspects 1 to 15, wherein the sensor is mounted to be above the plate work position and operatively adjacent a positioned plate held immediately therebelow in a plate platform, the positioned plate having its medium surface open upwardly.
17. An apparatus for locating the surface of a solid growth culture medium in a plate in a plate work position, the plate work position including a sensor and also having a datum level fixed in one dimension (z), wherein the sensor is capable of sensing the medium surface for the positioned plate and measuring the distance to the medium surface, the apparatus also including means for referencing the measured distance to the datum level to determine a surface positional reference, relative to the datum level, in one dimension (z) for the surface of the medium in the positioned plate.
18. An apparatus for locating the surface of a solid growth culture medium in a plate in a plate work position, the plate work position including a sensor and having a notional action line fixed in two dimensions (x, y) in a predetermined position and having a datum level fixed in one dimension (z), wherein the sensor is capable of sensing the medium surface within a sensing region for the positioned plate and measuring an average distance to the medium surface within that sensing region, the apparatus also including means for referencing the measured distance to the datum level to determine a surface positional reference relative to the datum level in one dimension (z) for the surface of the medium in the positioned plate and then using the surface positional reference and the notional action line to determine a line in three dimensions (x, y, z) that is representative of a line across the surface of the medium in the positioned plate.
19. An apparatus for locating the surface of a solid growth culture medium in a plate in a plate work position, the plate work position including a sensor and having a datum level fixed in one dimension (z), wherein the sensor has an upper limit and a lower limit to define a detection range between the upper and lower limits, and is capable of sensing, within the detection range, the medium surface for the positioned plate and measuring the distance to the medium surface, the apparatus including means for referencing the measured distance to the datum level to provide a surface positional reference relative to the datum level in one dimension (z) for the surface of the medium in the positioned plate.
20. An apparatus for locating the surface of a solid growth culture medium in a plate in a plate work position, the plate work position including a sensor and having a notional action line fixed in two dimensions (x, y) in a predetermined position and also having a datum level fixed in one dimension (z), wherein the sensor has an upper limit and a lower limit to define a detection range between the upper and lower limits, and is capable of sensing the medium surface, within the detection range, within a sensing region for the positioned plate and measuring an average distance to the medium surface within that sensing region, the apparatus including means for referencing the measured distance to the datum level to determine a surface positional reference relative to the datum level in one dimension (z) for the surface of the medium in the positioned plate, and then using the surface positional reference and the notional action line to determine a line in three dimensions (x, y, z) that is representative of a line across the surface of the medium in the positioned plate.
21. An apparatus according to any one of aspects 17 to 20, wherein the sensor is an ultrasonic sensing device that includes an ultrasonic beam focusing element that is capable of providing a focused beam on the medium surface.
22. An apparatus according to any one of aspects 17 to 21, wherein the sensor is rigidly mounted to a main frame, thereby defining the general location of the plate work position.
23. An apparatus according to any one of aspects 17 to 22, wherein the sensor is mounted to be above the plate work position and operatively adjacent a positioned plate held immediately therebelow in a plate platform, the positioned plate having its medium surface open upwardly.
24. A method according to aspect 1 substantially as herein described in relation to the accompanying figures.
25. A method according to aspect 6 substantially as herein described in relation to the accompanying figures.
26. A method according to aspect 7 substantially as herein described in relation to the accompanying figures.
27. A method according to aspect 13 substantially as herein described in relation to the accompanying figures.

28. An apparatus according to aspect 17 substantially as herein described in relation to the accompanying figures.
29. An apparatus according to aspect 18 substantially as herein described in relation to the accompanying figures.
30. An apparatus according to aspect 19 substantially as herein described in relation to the accompanying figures.
31. An apparatus according to aspect 20 substantially as herein described in relation to the accompanying figures.

In conclusion, it must be appreciated that there may be other variations and modifications to the configurations described herein which are also within the scope of the present invention.

We claim:

1. A method for automatically locating the surface of a solid growth culture medium in a plate in a plate work position, the plate work position having a datum level fixed in one dimension (z) and including a sensor fixed above and in place relative to a notional action line of the plate work position, the notional action line fixed in two dimensions (x, y) in a predetermined position, the method including:
automatically placing the plate in the plate work position such that the plate is positioned above the notional action line;
using the sensor to sense the medium surface within a sensing region of the notional action line for the positioned plate and measuring an average distance to the medium surface within that sensing region;
referencing the measured average distance to the medium surface to the datum level to determine a surface positional reference in one dimension (z) for the surface of the medium in the positioned plate;
combining the surface positional reference and the position of the notional action line to determine an action line in three dimensions (x, y, z) relative to the plate work position that is representative of a line across the surface of the medium in the positioned plate; and
providing the three-dimensional location of the action line to a robot pipetting system and/or an automated streaking device to permit the operative interaction of the robot pipetting system and/or the automated streaking device with the action line on the medium surface in the plate.

2. A method according to claim 1, wherein the surface of a medium in a plate, which plate is in its normal, generally horizontal orientation, is located in at least the z dimension by virtue of the determination of the surface positional reference.

3. A method according to claim 1, wherein the datum level is a surface that forms a part of a plate platform upon which the plate can be clamped and supported.

4. A method according to claim 1, wherein the determination of the surface positional reference determines the height of the medium with reference to the plate platform upon which it rests.

5. A method according to claim 1, wherein the sensor is an ultrasonic sensing device that includes an ultrasonic beam focusing element that is capable of providing a focused beam on the medium surface.

6. A method according to claim 1, wherein the sensor is rigidly mounted to a main frame, thereby defining the general location of the plate work position.

7. A method according to claim 1, wherein the sensor is mounted to be above the plate work position and operatively adjacent a positioned plate held immediately therebelow in a plate platform, the positioned plate having its medium surface open upwardly.

8. A method according to claim 1, wherein the operative interaction of the robot pipetting system and/or the automated streaking device comprises positioning the robot pipetting system and/or the automated streaking device at a position, relative to the plate, determined by the provided location of the action line.

9. An automated apparatus for locating the surface of a solid growth culture medium in a plate, the apparatus comprising:
a plate work position having a datum level fixed in one dimension (z) and including a sensor fixed above and in place relative to a notional action line of the plate work position, the notional action line fixed in two dimensions (x, y) in a predetermined position,
a plate transfer feed mechanism for positioning a culture plate on the plate work position above the notional action line,
a programmable controller connected to the sensor and to a robot pipetting system and/or an automated streaking device,
wherein the sensor is capable of sensing the medium surface within a sensing region of the notional action line and measuring an average distance from the sensor to the medium surface within the sensing region, when the plate is placed in the plate work position;
the sensor including a fixed datum point for referencing the measured average distance to the medium surface to the datum level to permit determination of a surface positional reference in one dimension (z) for the surface of the medium in the positioned plate; and
wherein the programmable controller determines the surface positional reference (z) for the surface of the medium in the positioned plate, relative to the datum level, combines the surface positional reference and the position of the notional action line to determine an action line in three dimensions (x, y, z) relative to the plate work position that is representative of a line across the surface of the medium in the positioned plate, and provides the three-dimensional location of the action line to the connected robot pipetting system and/or automated streaking device to permit the operative interaction of the robot pipetting system and/or the automated streaking device with the action line on the medium surface in the plate.

10. An apparatus according to claim 9, wherein the sensor is an ultrasonic sensing device that includes an ultrasonic beam focusing element that is capable of providing a focused beam on the medium surface.

11. An apparatus according to claim 9, wherein the sensor is rigidly mounted to a main frame, thereby defining the general location of the plate work position.

12. An apparatus according to claim 9, wherein the sensor is mounted to be above the plate work position and operatively adjacent a positioned plate held immediately therebelow in a plate platform, the positioned plate having its medium surface open upwardly.

* * * * *